United States Patent
Chadwick

[11] Patent Number: 5,360,770
[45] Date of Patent: Nov. 1, 1994

[54] FLUORIDE ION-LEACHABLE GLASSES AND DENTAL CEMENT COMPOSITIONS CONTAINING THEM

[75] Inventor: Thomas C. Chadwick, Nipomo, Calif.

[73] Assignee: Den-Mat Corporation, Santa Maria, Calif.

[21] Appl. No.: 817,885

[22] Filed: Jan. 7, 1992

[51] Int. Cl.$^5$ ............................................. C03C 8/08
[52] U.S. Cl. ......................................... 501/24; 501/30
[58] Field of Search .............. 106/35; 433/228.1; 501/13, 24, 30

[56] References Cited

U.S. PATENT DOCUMENTS

| | | | |
|---|---|---|---|
| 4,775,592 | 10/1988 | Akahane et al. | 428/406 |
| 4,808,228 | 2/1989 | Randklev | 106/35 |
| 4,900,697 | 2/1990 | Akahane et al. | 501/37 |
| 5,009,709 | 4/1991 | Ibsen et al. | 106/35 |
| 5,051,453 | 9/1991 | Okaybayashi et al. | 523/116 |
| 5,120,340 | 6/1992 | Ducheyne et al. | 65/18.3 |

FOREIGN PATENT DOCUMENTS 0241277 10/1987 European Pat. Off.
8815651 11/1988 WIPO.

Primary Examiner—Mark L. Bell
Assistant Examiner—A. Wright
Attorney, Agent, or Firm—Kazuyuki Yamasaki

[57] ABSTRACT

A glass composition, containing barium oxide, which provides a source of leachable fluoride and which can be incorporated into a dental cement composition which, when cured, is radiopaque and translucent.

20 Claims, No Drawings

FLUORIDE ION-LEACHABLE GLASSES AND DENTAL CEMENT COMPOSITIONS CONTAINING THEM

BACKGROUND OF THE INVENTION

1. Field of the Invention This invention relates to fluoride ion-leachable glasses and to water-or resin-based dental cement compositions containing such glasses.

2. Related Art

Aqueous poly (carboxylic acid) cement compositions are well known and have been routinely used in dentistry. Such compositions are commonly referred to as glass ionomer cements, and basically comprise (i) a polymer containing free carboxylic acid groups (typically a homo-or co-polymer of acrylic acid) and (ii) an ion-leachable glass such as calcium aluminofluorosilicate glass. In the presence of water, the glass leaches polyvalent metal ions such as aluminum and calcium ions and these serve to cross-link the polymer to give a rigid gelatinous structure. At the same time, silica material in the glass reacts with water to produce silicic acid. As a result of these gel-forming reactions, a cement, suitable for dental use, forms.

A problem with glass ionomer cements in the prior art is that they are radiolucent and thus provide no contrast on x-rays between the cement and surrounding tooth structure. In order to address this issue, it has been proposed to replace calcium in a calcium aluminofluorosilicate glass with strontium and, thereby, produce a glass which may be radiopaque, and still have acceptable properties with regard to strength, hardness, translucency, etc. (U.S. Pat. No. 4,814,362). The use of barium glass or barium sulphate to confer radiopacity on a glass ionomer has also been described (PCT application No. 88,105,651).

Calcium aluminofluorosilicate glass used in the glass ionomer cements contain large quantities of fluoride. Although fluoride lowers the firing temperatures of the glasses, it is also released in a cement composition where calcium aluminofluoro silicate is incorporated. Fluoride, if released in sufficient quantity, imparts carlostatic properties to the cements when used in the repair of carious lesions. However, while calcium aluminofluorosilicate glass is acceptable in terms of fluoride release, it is not desirable in dental use because of its visual opacity and limited radiopacity.

Thus, the requirement of adequate radiopacity and sustained fluoride release makes the development of new glasses desirable. Dental cement compositions containing such glasses should meet such other desirable criteria as: (a) translucency; (b) long shelf life; (c) low solubility in oral fluids; (d) strong adhesion to the tooth; (e) suitable working and setting times; and (f) adequate strength. The present invention provides fluoride ion-leachable glasses and dental cement compositions containing such glasses which meet these criteria.

SUMMARY OF THE INVENTION

It has now been found that certain alkaline earth metal aluminofluorosilicate glasses, in which the alkaline earth metal is one or more metals selected from the group consisting of calcium, strontium and barium, provide desired radiopacity, translucency, strength, hardness, etc.

According to this invention, there is provided a glass composition consisting essentially of the following components by molar percent:

| | |
|---|---|
| $SiO_2$ | 17.6–21.6 |
| $P_2O_5$ | 0.8–3.5 |
| $Al_2O_3$ | 9.0–11.0 |
| $Na_2O$ | 0.5–3.0 |
| MO | 7.9–19.7 |
| F | 42.2–56.1 | wherein MO is selected from the group consisting of BaO, BaO—CaO, BaO—SrO, and BaO—CaO—SrO.

According to this invention, there is also provided a dental cement composition comprising the above-defined glass together with dentally acceptable ingredients.

The glasses of this invention, when included in dental compositions, facilitate radiographic detection of caries in vivo, release fluoride in a controlled manner, and provide translucency to confer good esthetics to teeth.

DETAILED DESCRIPTION OF THE INVENTION

The glass composition of this invention may be prepared from a mixture of one or more alkaline earth metal fluorides, aluminum fluoride, alumina, silica, sodium fluoride and phosphorous pentaoxide. The alkaline earth metal fluoride is selected from the group consisting of calcium fluoride, barium fluoride and strontium fluoride. A preferred alkaline earth metal fluoride combination is barium fluoride alone, barium fluoride-calcium fluoride, strontium fluoride-barium fluoride, or calcium fluoride-barium fluoride-strontium fluoride.

Thus, suitable glass compositions include those having the following composition by molar percent (expressed as oxides except for fluoride):

| | |
|---|---|
| $SiO_2$ | 17.6–21.6 |
| $P_2O_5$ | 0.8–3.5 |
| $Al_2O_3$ | 9.0–11.0 |
| $Na_2O$ | 0.5–3.0 |
| MO | 7.9–19.7 |
| F | 42.2–56.1 | wherein MO is selected from the group consisting of BaO, BaO—CaO, BaO—SrO and CaO—BaO—SrO.

More specifically, the following glass composition is included:

| Composition | Molar % |
|---|---|
| $SiO_2$ | 20 |
| $P_2O_5$ | 2 |
| $Al_2O_3$ | 10 |
| $Na_2O$ | 2 |
| MO | 18 |
| F | 48 | wherein MO is as previously defined.

A variety of methods known in the art can be used to make the glass compositions of this invention. A typical procedure involves mixing of the required ingredients, melting and then cooling. The choice of starting materials used in this invention is not critical so long as the materials are substantially pure and provide desired metals.

The glass compositions of this invention wherein MO is BaO—CaO, BaO—SrO or CaO—BaO—SrO may be prepared by: (a) first forming calcium, barium and strontium glasses, respectively; (b) blending these glasses as required in appropriate amounts; and (c) further firing the mixture.

Alternatively, these binary or tertiary glass compositions can be prepared directly from appropriate starting materials. For example, the glass composition where MO is SrO—BaO can be prepared by blending silica, hydrated alumina, cryolite, aluminum fluoride, aluminum phosphate, strontium fluoride and barium fluoride and by firing the mixture. Regardless of the method of preparation employed, the resulting glass compositions will have substantially the same properties and characteristics.

Although barium fluoride, calcium fluoride, and strontium fluoride are specifically indicated as the source of the alkaline earth metals, these starting materials are exemplary and many other known salts derived from the alkaline earth metals can be used without adversely affecting the resulting glass compositions. Such suitable salts include barium carbonate, strontium carbonate, calcium carbonate, barium acetate, strontium acetate, and calcium acetate. When barium carbonate and strontium carbonate are used, these metal salts are conveniently reacted with hydrofluoric acid before being admixed with other ingredients.

The molar ratios of the alkaline earth metals can vary over a wide range. In a binary glass composition, the molar ratio of barium to calcium is preferably not less than 0.334, more preferably 1:1. The molar ratio of barium to strontium is preferably not less than 0.02, more preferably 1:1. In a tertiary glass composition, the molar ratio of barium to (calcium+strontium) is not less than 0.02 and the molar ratio of calcium to (barium+strontium) is not greater than 3.0. More preferably, barium, calcium, and strontium are present in equimolar quantities.

The glass composition of this invention may contain metal elements other than calcium, barium, and strontium, such as sodium, lithium, potassium and aluminum. The essential alkaline earth metals and other metals are derived from a variety of starting materials. In addition to calcium, barium and strontium salts enumerated above, aluminum fluoride, sodium fluoride, phosphoric acid, mono-, di- and tri-ammonium orthophosphate, calcium, dicalcium and tricalcium orthophosphates, alumina and hydrated alumina can be employed to provide for the metals, fluoride and phosphorous. However, it will be appreciated that the foregoing compounds are individually named for purposes of illustration and many other known materials in the art can be incorporated in the glass composition.

A critical feature of this invention is a high level of radiopacity of the glass composition. The glass composition wherein MO is BaO is especially radiopaque. Also, the glass composition wherein MO is BaO—SrO has high radiopacity. Particularly, the BaO—SrO glass composition wherein the molar ratio of combined barium and strontium to silica is greater than about 0.68 exhibits excellent radiopacity.

Another critical feature of this invention is increased translucency of the glass composition. Glass compositions wherein MO is BaO or BaO—SrO are particularly translucent. An especially preferred glass composition is the composition wherein MO is BaO. The glass compositions of this invention thus impart translucency to dental compositions which contain the glasses. Particularly, translucency is considered a property crucial to formulating methacrylate resin-based dental compositions.

A further critical feature of this invention is the ease of fluoride release from the dental cement compositions. Dental compositions based on glasses which are high in strontium or barium release fluoride at greater rates than dental compositions based on calcium glass. A particularly preferred dental composition is the composition which contains equimolar amounts of calcium, strontium and barium.

As indicated earlier, the glass compositions of this invention are suitable for use in water-or resin-based dental cement compositions. In order to prepare such dental compositions, the glass should be in particulate form and suitably has a particle size of from about 0.005 to about 500 microns.

Compositions for forming a dental cement from the glasses of this invention may conveniently assume a two-part form. A wide variety of ingredients can be used to make up the dental compositions and those in common use comprise a buffering agent, a bonding agent, a polymerizable matrix material, a hydrophilic resin, a polymerizable carboxylic acid, a thermal initiator, a photoinitator, a free-radical scavenger, and a coupling agent. Many other components such as pigments (iron oxide or titanium oxide) can be incorporated in the dental composition. Suitable components are, for example, described in U.S. Pat. No. 4,659,751 to R. L. Bowen, 4,674,980 to R. L. Ibsen et al., 4,746,686 to D. E. Waller, and 4,964,911 to R. L. Ibsen et al., , the disclosures of which are incorporated herein by reference.

The dental compositions of this invention prepared from the fluoride ion-leachable glasses possess translucency necessary for good esthetics, sustained fluoride releasing property to prevent caries formation and adequate radiopacity to provide good contrast of restorations to teeth on x-rays.

The invention will be described in further detail below by way of the embodiments thereof, but these embodiments should not be taken as limiting the scope of the invention. In the examples, all percentages are by weight unless otherwise stated.

Reagents

Calcium fluoride ($CaF_2$, minimum purity 97.5%), strontium fluoride ($SrF_2$, minimum purity 98%), barium fluoride ($BaF_2$, minimum purity 99.7%), silica ($SiO_2$, minimum purity 99%), hydrated alumina ($Al_2O_3.3H_2O$, minimum purity 98.6%), and cryolite ($Na_3AlF_6$, minimum purity 88.4%) were used for the preparation of the glasses. The composition of the aluminum fluoride was 92% $AlF_3$ and 8% $Al_2O_3$.

EXAMPLE 1

A base glass was prepared by mixing 34.8 parts by weight aluminum fluoride, 148.7 pads by weight hydrated alumina, 30.0 parts by weight cryolite, 464.8 parts by weight barium fluoride, 60 parts by weight aluminum phosphate, and 175 parts by weight silica.

The components were blended in baffled glass jars (4L or 19L depending on batch size) for one hour and the blended powders were then packaged in clay bonded silica glass crucibles for firing. The crucibles were heated as rapidly as possible (heating time was one hour for small batches and as long as 12 hours for large batches) to 1200° C. and then held at that temperature for three hours. At the end of the soak period, each crucible was removed from the furnace and the molten glass charge was poured into cold water contained in a stainless steel pan. Care was taken to pour the glass in a thin stream in order to provide extremely rapid cooling. The well-fractured glass was then dried overnight and ground in a ball mill to pass a 40-mesh U.S. Series screen.

The resulting glass powder had a composition in weight percent as follows:

| | |
|---|---|
| $Na_2O$ | 1.6 |
| $BaO$ | 47.2 |
| $Al_2O_3$ | 17.6 |
| $P_2O_5$ | 4.0 |
| $F$ | 16.1 |
| $SiO_2$ | 20.3 |
| Less O equivalent to F | <6.8> |

EXAMPLE 2

Powdered calcium glass (PREPARATION 1), 206 parts by weight, and powdered barium glass (EXAMPLE 1), 294 parts by weight, were blended in baffled mixing jars for one hour. The blends were then packed in clay bonded silica glass crucibles and fired rapidly to 1200° C. Heating took approximately 0.75 hours. The molten glasses were held at that temperature for 1.5 hours. After the holding period each crucible was removed from the furnace and the melt was poured rapidly in a thin stream into water. The well-fractured glass was washed, dried overnight and ground in a ball mill to pass a 40 mesh U.S. Series screen.

The composition of the resulting glass in weight percent was:

| | |
|---|---|
| $Na_2O$ | 1.8 |
| $CaO$ | 10.1 |
| $BaO$ | 27.8 |
| $Al_2O_3$ | 20.7 |
| $P_2O_5$ | 4.8 |
| $F$ | 18.9 |
| $SiO_2$ | 23.9 |
| Less O equivalent to F | <8.0> |

EXAMPLE 3

Powdered barium glass, 270.7 parts by weight, and powdered strontium glass (PREPARATION 2), 229.3 parts by weight, were blended and a binary glass was prepared according to EXAMPLE 2.

The composition of the resulting glass in weight percent was:

| | |
|---|---|
| $Na_2O$ | 1.7 |
| $BaO$ | 25.5 |
| $SrO$ | 17.2 |
| $Al_2O_3$ | 19.1 |
| $P_2O_5$ | 4.4 |
| $F$ | 17.4 |
| $SiO_2$ | 22.0 |
| Less O equivalent to F | <7.3> |

EXAMPLE 4

Powdered barium glass, 196.2 parts by weight, powdered strontium glass, 166.3 parts by weight, and powdered calcium glass, 137.6 parts by weight, were blended and a tertiary glass was prepared according to EXAMPLE 2.

The composition of the resulting glass in weight percent was:

| | |
|---|---|
| $Na_2O$ | 1.8 |
| $BaO$ | 18.5 |
| $SrO$ | 12.5 |
| $CaO$ | 6.8 |
| $Al_2O_3$ | 20.7 |
| $P_2O_5$ | 4.8 |
| $F$ | 19.0 |
| $SiO_2$ | 23.9 |
| Less O equivalent to F | <8.0> |

EXAMPLES 5-8

Dental cement compositions were prepared from the glass of EXAMPLE 1 by blending with suitable ingredients ascertainable to those skilled in the art. The glasses were wet milled prior to composite formulation. In a typical run, 800-900 cm³ of -40 U.S. Series glass powder was placed with the same volume of isopropyl alcohol in a 3.8L ball mill jar which was half filled with 10-12 mm diameter alumina balls. The mill was turned at 50 r.p.m. for 50 hours and the mill contents were then screened through a course screen. The glass-alcohol slurry was then air and oven dried (110° C.) to constant weight for use in composite formulation. The resulting glass powder was mixed with appropriate ingredients to produce two component composite formulations.

The resin base used to formulate Part A of the test composites consisted of approximately equal amounts of an aromatic dimethacrylate oligomer and 2-hydroxyethyl methacrylate along with small amount of benzoyl peroxide and a polymerization inhibitor. Part B resin consisted principally of an aromatic dimethacrylate oligomer along with small amounts of a photoinitiator and a chelating agent. Because of the differing densities of the test glasses, the weight of glass in each composite had to be adjusted to maintain a constant volume fraction of filler glass in the finished composite. The test composite formulations are shown in the table below where glass and resin are expressed as parts by weight.

| CEMENT | GLASS | PART A | | PART B | |
|---|---|---|---|---|---|
| | | GLASS | RESIN | GLASS | RESIN |
| | PREPARATION 1 | 54.1 | 45.9 | 52.1 | 47.9 |
| | PREPARATION 2 | 57.3 | 42.7 | 55.4 | 44.6 |
| EXAMPLE 5 | EXAMPLE 1 | 60.6 | 39.4 | 58.8 | 41.2 |
| EXAMPLE 6 | EXAMPLE 2 | 56.8 | 43.2 | 54.9 | 45.1 |
| EXAMPLE 7 | EXAMPLE 3 | 58.5 | 41.5 | 56.6 | 43.4 |

| CEMENT | GLASS | PART A | | PART B | |
| --- | --- | --- | --- | --- | --- |
| | | GLASS | RESIN | GLASS | RESIN |
| EXAMPLE 8 | EXAMPLE 4 | 56.7 | 43.3 | 54.8 | 45.2 |

Composite test specimens were prepared from the two components A and B by mixing them together in a ratio by weight of about 1:1. The mixture was cured by exposure to a dental curing light for about 30 seconds (Visar curing light, Den-Mat, Inc., Santa Maria, Calif.).

Fluoride release from each composite was evaluated using a modification of the procedure described by Wilson, et al., Biomaterials, 1985, 6, 431. Eight specimens discs for each composite were prepared by mixing equal parts of the A and B components and pressing the mixture into 2 mm×20 mm (diam) molds. A piece of unwaxed dental floss was inserted in one edge of each disc to provide a means for suspending the specimen in the leaching solution. The mold faces were then covered with Saran ® sheets, pressed between glass slabs and cured for 30 seconds with a strong light.

The test specimens were then suspended in a circular arrangement from the snap lid of a 250 mL polyethylene container by securing their suspending dental floss cords to the lid with dabs of hot melt adhesive.

Fluoride release for each composite was followed by suspending the eight specimen discs in 100 mL aliquots of distilled water. The water was changed at the time intervals suggested by Wilson, et al. and the fluoride content of each sample was measured with an Orion Fluoride ion-selective electrode after quantitative dilution (1:1 v/v) of the leach solution with a pH 5.0–5.5 buffer that was 1.00M in NaCl and 1.00M in total acetate (sodium acetate and acetic acid). The fluoride electrode was calibrated with suitable standards which also contained the same buffer as the specimens. Fluoride release was expressed as mcg fluoride/mm$^2$ of composite surface area. Release data were evaluated by plotting log (cumulative fluoride release) versus log (total elapsed time).

Visual translucency was evaluated by comparing 0.5×20 mm (diam) composite disc to each other and to opal glass standards with $C_{0.70}$ values of 0.35 and 0.55 using the black and white background specified by the ASC MD 156 Task Group of the American Dental Association [Task Group on Posterior Composites "Procedure Protocol —Physical Chemical and Degradation Properties", American Dental Association, Chicago, 1989, 5].

Radiopacity was evaluated using the procedure described in ISO Standard 4049. [Technical Committee ISO/TC101, International Standard 150, 4049, International Organization for Standardization 1988. Sec. 7.11]

Radiopacity was evaluated by visually comparing the optical density of x-ray images of composite samples which had been placed on the same piece of dental x-ray film. A 2.0 mm thick Al standard was used as a control. The various cement composites were then ranked according to decreasing radiopacity as follows:
Radiopacity The composite of EXAMPLE 5 > The composite of EXAMPLE 7 > The composite of EXAMPLE 6 > The composite of EXAMPLE 8 > A cement composite made from the glass of PREPARATION 1.

Samples were evaluated for visual opacity by the ADA Posterior Composite Task Group procedure as described above. Sample chips were ranked in order of opacity as follows:
Visual Opacity The composite of EXAMPLE 5 < The composite of EXAMPLE 7 < The composite of EXAMPLE 8 < The composite of EXAMPLE 6 < A composite made from the glass of PREPARATION 1.

Fluoride release test data is provided in the following table.

| Composite | Cumulative Fluoride Release (40 days) mcg/mm$^2$ |
| --- | --- |
| A cement composite made from the glass of PREPARATION 1 | 0.108 |
| The composite of EXAMPLE 5 | 0.127 |
| The composite of EXAMPLE 6 | 0.175 |
| The composite of EXAMPLE 7 | 0.188 |
| The composite of EXAMPLE 8 | 0.266 |

It will be readily seen from the above data that the glasses of this invention and the dental cements derived therefrom show great fluoride release rates and are also radiopaque and translucent.

PREPARATION 1

A base glass was prepared according to EXAMPLE 1 but using 207 parts by weight calcium fluoride instead of barium fluoride. The composition of the finished base glass in weight percent was:

| | |
| --- | --- |
| Na$_2$O | 2.2 |
| CaO | 24.6 |
| Al$_2$O$_3$ | 25.1 |
| P$_2$O$_5$ | 5.8 |
| F | 23.0 |
| SiO$_2$ | 29.0 |
| Less O equivalent to F | <9.7> |

PREPARATION 2

A base glass was prepared according to EXAMPLE 1 but using 333 parts by weight strontium fluoride instead of barium fluoride. The composition of the finished base glass in weight percent was:

| | |
| --- | --- |
| Na$_2$O | 1.8 |
| SrO | 37.6 |
| Al$_2$O$_3$ | 20.8 |
| P$_2$O$_5$ | 4.8 |
| F | 19.0 |
| SiO$_2$ | 24.0 |
| Less O equivalent to F | <8.0> |

Although particular embodiments of this invention have been disclosed herein for purposes of explanation, further modifications or variations thereof will be apparent to those skilled in the art to which this invention pertains.

I claim:

1. A glass composition consisting essentially of the following ingredients by molar percent:

| | |
|---|---|
| $SiO_2$ | 17.6–19.7 |
| $P_2O_5$ | 0.8–3.5 |
| $Al_2O_3$ | 9.0–11.0 |
| $Na_2O$ | 0.5–3.0 |
| MO | 17.9–19.7 |
| F | 42.2–56.1 | wherein MO is selected from the group consisting of BaO, BaO—CaO, BaO—SrO, and BaO—CaO—SrO.

2. The glass composition according to claim 1, wherein MO is BaO—CaO.

3. The glass composition according to claim 2, wherein the molar ratio of BaO to CaO is not less than 0.334.

4. The glass composition according to claim 3, wherein the molar ratio of BaO to CaO is 1:1.

5. The glass composition according to claim 1, wherein MO is BaO—SrO.

6. The glass composition according to claim 5, wherein the molar ratio of BaO to SrO is not less than 0.02.

7. The glass composition according to claim 6, wherein the molar ratio of BaO to SrO is 1:1.

8. The glass composition according to claim 1, wherein MO is BaO—CaO—SrO.

9. The glass composition according to claim 8, wherein the molar ratio of BaO to (CaO+SrO) is not less than 0.02 and the molar ratio of CaO to (SrO+BaO) is not greater than 3.0.

10. The glass composition according to claim 9, wherein the molar ratio of BaO—CaO—SrO is 1:1:1.

11. A glass composition consisting essentially of the following ingredients by molar percent:

| | |
|---|---|
| $SiO_2$ | 20 |
| $P_2O_5$ | 2 |
| $Al_2O_3$ | 10 |
| $Na_2O$ | 2 |
| MO | 18 |
| F | 48 | wherein MO is selected from the group consisting of BaO, BaO—CaO, BaO—SrO, and BaO—CaO—SrO.

12. The glass composition according to claim 11, wherein MO is BaO.

13. The glass composition according to claim 11, wherein MO is BaO—CaO.

14. The glass composition according to claim 13, wherein the molar ratio of BaO to CaO is not less than 0.334.

15. The glass composition according to claim 14, wherein the molar ratio of BaO to CaO is 1:1.

16. The glass composition according to claim 11, wherein MO is BaO—SrO.

17. The glass composition according to claim 16, wherein the molar ratio of BaO to SrO is not less than 0.02.

18. The glass composition according to claim 17, wherein the molar ratio of BaO to SrO is 1:1.

19. The glass composition according to claim 11, wherein MO is BaO—CaO—SrO.

20. The glass composition according to claim 19, wherein the molar ratio of BaO to (CaO+SrO) is not less than 0.02 and the molar ratio of CaO to (SrO+BaO) is not greater than 3.0.

* * * * *